United States Patent [19]

McColl et al.

[11] 3,993,705

[45] Nov. 23, 1976

[54] CHLORINATED HYDROCARBONS

[75] Inventors: Ian Stuart McColl; Ashley Cedric Pardoe Pugh, both of Runcorn, England

[73] Assignee: Imperial Chemical Industries Limited, London, England

[22] Filed: Mar. 7, 1975

[21] Appl. No.: 556,419

[30] Foreign Application Priority Data
Mar. 22, 1974 United Kingdom............ 12799/74

[52] U.S. Cl............................. 260/654 D; 260/654 S
[51] Int. Cl.²........................................ C07C 21/08
[58] Field of Search.......... 260/652 P, 654 S, 654 D

[56] References Cited
UNITED STATES PATENTS

| | | | |
|---|---|---|---|
| 2,418,109 | 4/1947 | Sconce | 260/654 S |
| 3,595,928 | 7/1971 | Rideout et al. | 260/654 S |
| 3,725,486 | 4/1973 | McCracken et al. | 260/654 D |
| 3,751,495 | 8/1973 | Seyferth | 260/654 D |

*Primary Examiner*—D. Horwitz
*Assistant Examiner*—Joseph A. Boska
*Attorney, Agent, or Firm*—Cushman, Darby & Cushman

[57] ABSTRACT

Vinylidene chloride containing dichloroacetylene as an impurity is purified by treatment with a solution of a sulphide, polysulphide or hydrosulphide, for example an aqueous solution of ammonium hydrosulphide, sodium hydrosulphide or potassium hydrosulphide. The impure vinylidene chloride may be treated with the solution of sulphide, hydrosulphide, or polysulphide after isolation from the reaction mixture in which it is formed, or the vinylidene chloride may be treated in situ in the reaction mixture before isolation.

12 Claims, No Drawings

CHLORINATED HYDROCARBONS

This invention relates to a process for the purification of chlorinated hydrocarbons and more particularly to a process for the purification of vinylidene chloride.

Vinylidene chloride may be prepared by the dehydrochlorination of 1,1,2-trichloroethane, and known dehydrochlorinating agents for this reaction include milk-of-lime and aqueous alkali metal hydroxide solutions. Dehydrochlorination of 1,1,2-trichloroethane (and more particularly of impure 1,1,2-trichloroethane containing other chlorinated hydrocarbons such as tetrachloroethane or chloroethylenes) may lead to the formation of chloroacetylenes (especially dichloroacetylene) in addition to the desired vinylidene chloride product. The formation of chloroacetylenes is particularly likely to occur when aqueous alkali metal hydroxide solution is used as the dehydrochlorinating agent.

Choroacetylenes are undesirable because they are both toxic and explosive. Furthermore vinylidene chloride containing chloroacetylenes tends to become discoloured on standing. Dichloroacetylene is especially troublesome because is is much more difficult to separate from vinylidene chloride by fractional distillation.

We have now found that the concentration of dichloroacetylene in impure vinylidene chloride may be substantially reduced by the addition of a soluble sulphide, polysulphide or hydrosulphide, either to the impure vinylidene chloride itself or during its manufacture.

Thus according to the present invention there is provided a process for the removal of dichloroacetylene impurities from impure vinylidene chloride which comprises treating the said impure vinylidene chloride with a solution of a sulphide, polysulphide or hydrosulphide.

Preferred sulphides, polysulphides or hydrosulphides are those of ammonia or a metal (for example a metal in Group Ia or IIa in the Periodic Table). Especially preferred are ammonium hydrosulphide and the hydrosulphides of sodium, calcium and potassium. Mixtures of metal or ammonium sulphides, polysulphides or hydrosulphides may be used if desired. Preferably the sulphide, polysulphide or hydrosulphide is present in aqueous solution. In aqueous solution a metal sulphide may undergo partial or complete hydrolysis to form the hydrosulphide.

The process of the present invention is particularly suitable for the treatment of impure vinylidene chloride produced by the dehydrochlorination of 1,1,2-trichloroethane with aqueous alkali metal hydroxide solution, but may be used for the treatment of vinylidene chloride from a variety of sources contaminated with a wide range of concentrations of dichloroacetylene including for example (but not restricted to) the range from 2 ppm by weight to 5% by weight.

The impure vinylidene chloride may be treated with the solution of sulphide, hydrosulphide or polysulphide subsequently to its isolation from the reaction mixture in which it is formed, or the vinylidene chloride may be treated in situ in in the reaction mixture. When the vinylidene chloride is manufactured by the dehydrochlorination of 1,1,2-trichloroactylene, for example with aqueous alkali metal hydroxide solution, the sulphide, hydrosulphide or polysulphide may be present during the dehydrochlorination itself and used to treat the impure vinylidene chloride as it is formed during manufacture.

The concentration of the solution of the sulphide, polysulohide or hydrosulphide, used to tqe[t impure vinylidene chloride may be varied within wide limits. The concentration of the sulphide, polysulphide or hydrosulphide is conveniently measured in tdrms of the total sulphur present in any or all of these three forms and expressed as grams of sulphur per 100 grams of solution. This concentration may for example vary from 0.5 to 20 grams sulphur per 100 grams solution, the higher proportions being preferred for high concentrations of dichloroacetylene though higher or lower concentrations may be used if desired.

The purification of impure vinylidene chloride may be performed in a variety of ways. For example the treatment of impure vinylidene chloride with the sulphide, polysulphide or hydrosulphide may take place as either a continuous or a batch process, and may take place in one or more reaction vessels. The impure vinylidene chloride may be treated in either the liquid phase or the vapour phase.

In a batch process it is preferred to contact a single volume of sulphide, polysulphide or hydrosulphide solution successively with a number of separate charges of impure vinylidene chloride, separating the purified vinylidene chloride from the said solution after each addition. The number of charges of impure vinylidene chloride which may be effectively treated by a single volume of sulphide, polysulphide or hydrosulphide or hydrosulphide solution will depend on several factors, including for example the concentration and volume of the sulphide, polysulphide or hydrosulphide employed and the concentration of dichloroacetylene impurity present in the vinylidene chloride. Typically a single volume of sulphide, polysulphide or hydrosulphide solution might be capable of treating of the order of 20 batches of impure vinylidene chloride.

In a continuous process it is similarly preferred to employ a flow of sulphide, polysulphide or hydrosulphide solution into the reactor which is less than the flow of impure vinylidene chloride. Again the preferred ratio of flows will depend on similar factors, but typically the flow of impure vinylidene chloride might, for example be of the order of 20 times greater than the flow of sulphide, polysulphide or hydrosulphide.

The volume of sulphide, polysulphide or hydrosulphide solution present in the reactor (in either a batch or continuous process) relative to the volume of impure vinylidene chloride is not critical, but it is convenient, for example, to employ substantially equal volumes of the sulphide, polysulphide or hydrosulphide solution and the impure vinylidene chloride in the reactor.

To increase the contact between the impure vinylidene chloride and the sulphide, polysulphide or hydrosulphide, it is preferred to stir or agitate their mixture. The preferred time for which the sulphide, polysulphide or hydrosulphide solution and the impure vinylidene chloride are in contact (in either a batch or continuous process) will depend on a number of factors including the particular sulphide, polysulphide or hydrosulphide used, its concentration in solution, the temperature and the rate of stirring of the mixture. The contact time which is sufficient to substantially remove the chloroacetylene impurity may be determined by simple trial. It is preferred to avoid an excessively long total residence time of the sulphide, polysulphide or hydrosulphide solution in the system (for example a residence time greater than 60 hours).

When the vinylidene chloride is treated with the sulphide, polysulphide or hydrosulphide solution in the liquid phase, temperatures up to the boiling point of the impure vinylidene chloride (for example a temperature of 0° C to 32°) may be used. The treatment conveniently takes place at room temperature.

Alternatively or additionally, the impure vinylidene chloride may be vapourised and the vapour treated with the (liquid phase) solution of the sulphide, hydrosulphide or polysulphide at a temperature below the boiling point of the solution (for example a temperature of 32° C to 100° C and especially a temperature of 60° to 95° C). For example the impure vinylidene chloride may be vapourised and the vapour passed to a packed column irrigated with a counter-current flow of the hot solution. The impure vinylidene chloride may be vapourised directly from the reaction mixture in which it is found or the impure vinylidene chloride may be isolated from the reaction mixture and subsequently vapourised.

When the treatment of the impure vinylidene chloride with the sulphide, polysulphide or hydrosulphide solution is complete (or continuously during the course of such treatment), it is preferred to separate the purified vinylidene chloride from the liquid phase (for example the aqueous phase) in which the sulphide, polysulphide or hydrosulphide is dissolved. Said separation may take place by simple and conventional means, for example by direct phase separation.

In an alternative embodiment of the present invention, the sulphide hydrosulphide or polysulphide may be used to treat the impure vinylidene chloride as it is formed during manufacture.

Thus according to a further aspect of the present invention there is provided a process for the manufacture of vinylidene chloride which comprises dehydrochlorinating 1,1,2-trichloroethane in the presence of a solution of a sulphide, polysulphide or hydrosulphide.

Vinylidene chloride when conventionally prepared by the dehydrochlorination of 1,1,2-trichloroethane (for example with aqueous alkali metal hydroxide solution) may contain a wide range of concentrations of dichloroacetylene.

Thus the concentration of dichloroacetylene typically varies from 2 ppm by weight to 600 ppm by weight depending on the purity of the 1,1,2-trichloroethane and mode of operation of the process. When sulphide, polysulphide or hydrosulphide is present during the dehydrochlorination of 1,1,2-trichloroethane, the concentration of sulphide, polysulphide or hydrosulphide necessary to limit the formation of dichloroacetylene is capable of a correspondingly wide variation. Thus the concentration of sulphide, polysulphide or hydrosulphide in solution (expressed as described above, as 'grams of sulphur per litre of solution') may for example vary from 0.08 to 1.5 gram of sulphur per litre of the solution of the dehydrochlorinating agent. Higher concentrations (for example 15 grams of sulphur per litre) may be used if an especially pure vinylidene chloride product is required, and lower concentrations (for example 0.01 gram of sulphur per litre) may be used if the concentration of dichloroacetylene to be removed is not expected to be large (for example when the trichloroethane feedstock is relatively free from impurities). The optimum concentration of sulphide, or hydrosulphide necessary to limit the formation of dichloroacetylene under any particular operating conditions may be determined by simple trial.

In the process of the present invention the 1,1,2-trichloroethane starting material need not necessarily be pure. Indeed it is an advantageous feature of the present process that crude 1,1,2-trichloroethane can be used as organic feedstock to produce vinylidene chloride of good quality and low dichloroacetylene content. Such crude 1,1,2-trichloroethane can be contaminated with appreciable proportions, for example up to 10% by weight or more for example up to 30% by weight of other chloroethanes and chloroethylenes.

The dehydrochlorination of the 1,1,2-trichloroethane in the presence of the sulphide, polysulphide or hydrosulphide may take place over a wide range of temperatures as it is already known in the art, but particularly useful results are obtained within the range 75° to 90° C, especially 75° to 85° C.

The operation of the present invention is not limited by the concentration or pH of the dehydrochlorination agent, and when using an aqueous solution of sodium hydroxide as dehydrochlorinating agent for example, the hydroxyl ion concentration may range from 0.001N to 5N, but is commonly 0.01N to 0.1N.

When the dehydrochlorination of the 1,1,2-trichloroethane is complete, or in progress, an organic phase containing the vinylidene chloride product is usually separated from the aqueous phase in conventional manner. A proportion of the sulphide, polysulphide or hydrosulphide originally present in solution is removed by a reaction which substantially removes dichloroacetylene as it is formed during the dehydrochlorination reaction. However the aqueous phase separated from the vinylidene chloride product will generally contain some unchanged sulphide, polysulphide or hydrosulphide. The sulphide, polysulphide or hydrosulphide may be recovered if desired, but it is generally more convenient to send the aqueous stream directly to waste.

The optimum concentration or proportion of the sulphur compound in any particular instance can be determined by simple trial, taking into account such factors as the purity of the raw materials, the reaction conditions, the purity required in the product, and the amounts of sulphur compound which can acceptably be run to waste. In some circumstances, for example when it is considered undesirable to discharge much of the sulphur compound to waste, it may be convenient to carry out the treatment process of our invention in several stages, for example by treating impure vinylidene chloride with the sulphur compound in two or more successive stages or by adding some of the solution of sulphide, hydrosulphide or polysulphide to the dehydrochlorination reactor and then subjecting the vinylidene chloride product to treatment with a solution of sulphide, hydrosulphide or polysulphide to purify it still further. The latter solution may if desired be subsequently used in the dehydrochlorination reactor.

It is a particular advantage of the present process for the manufacture or purification of vinylidene chloride that the product of the reaction between the chloroacetylene and the sulphide, polysulphide or hydrosulphide are soluble in water. Such products are therefore partially or completely removed from the organic phase during the treatment with an aqueous phase.

It is a further advantage of the present process that the reaction product of the dichloroacetylene and the sulphide, polysulphide or hydrosulphide has a significantly lower vapour pressure than vinylidene chloride. Any reaction product remaining is therefore readily separated from the vinylidene chloride during any subsequent fractional distillation stage.

When the dichloroacetylene impurity has been removed, the vinylidene chloride may be further purified by conventional means, for example by fractional distillation. Any residue of monochloroacetylene may be safely removed by conventional means, for example by passing the liquid vinylidene chloride product down a tube continuously purged with nitrogen.

The vinylidene chloride from which the dichloroacetylene impurity has been removed may be used (either with or without further purification) as a raw material for a further reaction. Thus the vinylidene chloride may, for example be hydrochlorinated to produce 1,1,1-trichloroethane. Any danger of the formation of explosive mixtures of chloroacetylene and vinylidene chloride during the distillation of unreacted vinylidene chloride from the product will have been substantially reduced by the removal of the dichloroacetylene.

The invention is illustrated by the following Examples in which the parts and percentages are by weight unless otherwise stated.

EXAMPLE 1

Impure vinylidene chloride containing dichloroacetylene at a concentration of 327 parts per million was treated with an equal volume of an aqueous solution containing 100 grams of sodium hydrosulphide per litre. The mixture was agitated continuously, and after 1 hour the concentration of dichloroacetylene in the vinylidene chloride had fallen to 74 parts per million.

EXAMPLE 2

Impure vinylidene chloride containing dichloroacetylene at a concentration of 308 parts per million was treated with an equal volume of an aqueous solution containing 81 grams of sodium sulphide per litre. The mixture was agitated continuously, and after 1 hour the concentration of dichloroacetylene in the vinylidene chloride had fallen to 135 parts per million.

EXAMPLE 3

Impure vinylidene chloride containing dichloroacetylene at a concentration of 100 parts per million was treated with an equal volume of an aqueous solution containing 100 grams of calcium hydrosulphide per litre. The mixture was agitated continuously, and after 40 minutes the concentration of dichloroacetylene in the vinylidene chloride had fallen to 38 parts per million.

EXAMPLE 4

Impure vinylidene chloride containing dichloroacetylene at a concentration of 100 parts per million was treated with an equal volume of an aqueous solution containing 100 grams of ammonium sulphide per litre. The mixture was agitated continuously, and after 20 minutes the concentration of dichloroacetylene in the vinylidene chloride had fallen to 8 parts per million.

EXAMPLE 5

Impure vinylidene chloride containing dichloroacetylene at a concentration of 100 parts per million was treated with an equal volume of an aqueous solution containing 100 grams of potassium hydrosulphide per litre. The mixture was agitated continuously, and after 30 minutes the concentration of dichloroacetylene in the vinylidene chloride had fallen to 29 parts per million.

EXAMPLE 6

Vinylidene chloride contaminated with 220 ppm of dichloroacetylene and an aqueous solution containing 10% of sodium hydrosulphide were separately and continuously fed into a stirred reactor. The liquid mixture was pumped from the reactor, via a capillary tube to a separator vessel in which the mixture separated into an upper, aqueous layer and a lower layer comprising the purified vinylidene chloride. The purified vinylidene chloride passed out of the system at the same rate as that at which the impure product entered the reactor. A portion of the upper, aqueous layer was drawn off from the system by a peristaltic pump at the same rate as that at which the fresh solution of sodium hydrosulphide entered the reactor, whilst the remainder of of the aqueous layer overflowed from the separator and was returned to the reactor.

The impure vinylidene chloride was fed into the reactor at a rate of 64 mls/hr and the fresh sodium hydrosulphide solution at a rate of 3.2 mls/hr. The volume of vinylidene chloride present in the reactor at any given time was approximately 85 mls, and that of the sodium hydrosulphide was also approximately 85 mls.

The reactor was operated continuously for 48 hours, and the concentration of dichloroacetylene measured in the purified vinylidene chloride product (measured at intervals of approximately 6 hours) ranged from 37 ppm to 54 ppm with an average value of 50 ppm. This corresponded to a 78% reduction in the concentration of dichloroacetylene.

EXAMPLE 7

Vinylidene chloride was prepared by the dehydrochlorination of 1,1,2-trichloroethane with aqueous sodium hydroxide solution. The apparatus was designed to correspond on a smaller scale the industrial manufacture of vinylidene chloride by this method.

1,1,2-trichloroethane containing tetrachloroethylene as a impurity was continuously fed into a stirred reactor maintained at a temperature of 80° C. An aqueous solution containing sodium hydroxide and sodium hydrosulphide was separately fed into the reactory where the aqueous and organic phases become well mixed. In addition to the desired product (vinylidene chloride), the products of the dehydrochlorination were found to include trichloroethylene and dichloroacetylene.

Organic vapours containing the reactants and products passed from the reactor to a packed distillation column and reflux condenser, the latter being maintained at approximately 50° C. Unreacted 1,1,2-trichloroethane and tetrachloroethylene were thereby condensed and returned to the reactor. Vinylidene chloride, trichloroethylene and dichloroacetylene passed through the reflux condenser and were subsequently condensed by a product condenser maintained at approximately 12° C.

An overflow was provided in the reactor whereby the liquid phases contained therein passed continuously out of the reactor, through a stripper column to a heater vessel. The organic species flowing into the said heated vessel were vapourised, and the vapours, after passing (in counter-flow to the liquid from the reactor) through the stripper column, were returned to the reactor. The aqueous phase overflowed from the heated vessel, and in this way the aqueous product stream was substantially separated from any organic species, the latter being returned as vapour to the reactor, as hereinbefore described.

At intervals samples were withdrawn from the product stream and the concentration of dichloroacetylene in the vinylidene chloride product was measured by gas-liquid chromatography. Simultaneously samples were withdrawn from the aqueous product stream, and the concentration of sodium hydroxide therein was measured by titration with standard acid.

1,1,2-trichloroethane containing 4.7% of tetrachloroethane was fed into the reactor at a rate of 57.6 mls/hr. Simultaneously an aqueous solution containing 1 mole per litre of sodium hydroxide and 0.45 gram per litre of sodium hydrosulphide was fed into the reactor at various selected rates. Measurements were made at each of the selected flow-rates of the aqueous reactants and it was found that the concentration of sodium hydroxide in the aqueous phase leaving the system varied over the range from 0.05 to 0.17 mole per litre.

The concentration of dichloroacetylene measured in the vinylidene chloride product was found to vary as a linear function of the hydroxyl ion concentration in the aqueous phase in the reactor (the latter being equivalent to the concentration of sodium hydroxide in the aqueous phase leaving the system). The concentration of dichloroacetylene in the vinylidene chloride product was found to be 56 parts per million when the aqueous solution leaving the reactor contained sodium hydroxide at a concentration of 0.1 mole per litre.

For comparison, the procedure of the Example was repeated using the same concentrations, flow-rates and conditions, but in the absence of sodium hydrosulphide. The concentration of dichloroacetylene measured in the vinylidene chloride product was again found to vary as a linear function of the hydroxyl ion concentration in the aqueous phase in the reactor. However the concentration of dichloroacetylene in the vinylidene chloride was much greater and was now found to be 510 parts per million when the aqueous solution leaving the reactor contained sodium hydroxide at a concentration of 0.1 mole per litre.

Addition of sodium hydrosulphide had therefore achieved an 89% reduction in the concentration of dichloroacetylene in the vinylidene chloride product.

What we claim is:

1. A process for the removal of dichloroacetylene impurities from impure vinylidene chloride which comprises treating the said impure vinylidene chloride with a solution of a compound selected from the group consisting of a sulphide, polysulphide or hydrosulphide of ammonia or of a metal in Group IA or IIA of the Periodic Table or a mixture of two or more thereof.

2. A process according to claim 1 wherein the impure vinylidene chloride is treated with a solution of a compound selected from the group consisting of ammonium hydrosulphide, sodium hydrosulphide, calcium hydrosulphide and potassium hydrosulphide.

3. A process according to claim 1 wherein the concentration of the said compound, expressed as grams of sulphur per 100 grams of solution, is from 0.5 to 20 grams per 100 grams of solution.

4. A process according to claim 1 wherein the vinylidene chloride is treated in the liquid phase.

5. A process according to claim 4 wherein the temperature is 0° C to 32° C.

6. A process according to claim 1 wherein the vinylidene chloride is treated in the vapour phase with a liquid phase solution of the said compound.

7. A process according to claim 6 wherein the temperature is from 60° to 95° C.

8. A process for the manufacture of vinylidene chloride which comprises dehydrochlorinating 1,1,2-trichloroethane containing chlorinated hydrocarbons which lead to the formation of chloroacetylenes in the presence of a solution of a compound selected from the group consisting of a sulphide, polysulphide or hydrosulphide of ammonia or of a metal in Group IA or IIA of the Periodic Table or a mixture of two or more thereof whereby the vinylidene chloride, as it is formed, is treated by a process according to claim 1.

9. A process according to claim 8 wherein the concentration of the said compound, expressed as grams of sulphur per litre of solution of dehydrochlorinating agent, is 0.01 to 15 grams per litre.

10. A process according to claim 9 wherein the concentration is 0.08 to 1.5 grams per litre.

11. A process according to claim 8 wherein the temperature is from 75° to 85° C.

12. A process according to claim 8 wherein the temperature is from 75° to 90° C.

* * * * *